United States Patent [19]

Waarvik

[11] Patent Number: 4,683,207

[45] Date of Patent: Jul. 28, 1987

[54] CULTURE MONITORING SYSTEM

[75] Inventor: Thomas L. Waarvik, Indianapolis, Ind.

[73] Assignee: Eli Lilly and Company, Indianapolis, Ind.

[21] Appl. No.: 678,295

[22] Filed: Dec. 5, 1984

[51] Int. Cl.[4] ............................................. C12M 1/12
[52] U.S. Cl. ................................. 435/311; 435/316; 422/101
[58] Field of Search ............... 435/292, 290, 293, 311, 435/316, 808; 264/28; 422/101, 103; 137/590

[56] References Cited

U.S. PATENT DOCUMENTS

| | | | |
|---|---|---|---|
| 3,291,184 | 12/1966 | Varvel | 137/590 |
| 3,551,297 | 12/1970 | Hosler | 435/311 |
| 3,647,632 | 3/1972 | Johnson et al. | 435/311 |
| 4,247,498 | 1/1981 | Castro | 264/28 |
| 4,596,779 | 6/1986 | Ono | 435/311 |

FOREIGN PATENT DOCUMENTS

| | | | |
|---|---|---|---|
| 0073079 | 3/1983 | European Pat. Off. | 435/311 |
| 95879 | 6/1984 | Japan | 435/311 |
| 232085 | 11/1985 | Japan | 435/311 |
| 798174 | 1/1981 | U.S.S.R. | 435/311 |

Primary Examiner—James C. Yeung
Attorney, Agent, or Firm—Barnes & Thornburg

[57] ABSTRACT

A system for continuously monitoring the chemistry of a liquid medium within a container includes assaying instrumentation located exteriorly of the container, a conduit connected to the assaying instrumentation and leading to the container, a probe connected to the conduit and penetrating a wall of the container. The probe includes a microporous filtering element for separating a filtrate from the culture medium, the filtering element having a surface roughness less than about 50 microinches.

11 Claims, 2 Drawing Figures

CULTURE MONITORING SYSTEM

The present invention relates generally to apparatus for measuring or testing the chemical, biochemical and physical properties of the soluable filtrate existing in a fermenter media and particularly to apparatus for continuously monitoring the same within a contained recombinant DNA system.

Industrial fermentation is employed in the production of many products including solvents, organic acids, modified carbohydrates, vitamins, amino acids, antibiotics, and enzymes. Of particular interest in recent years has been the production of pharmaceutical products utilizing inoculants having modified genetic structure achieved through recombinant DNA processes.

In all industrial fermentation processes, it is desirable to monitor the chemistry of the growth medium so as to ensure optimum conditions for the desired microbial action. This monitoring can be satisfied in many conventional industrial processes by periodic sampling of the medium. With the presence of new or at least modified organisms achieved through recombinant DNA procedures, it is mandatory that the microorganisms involved not be permitted to escape into the general environment. Certain procedures and requirements have been established to ensure contained systems for handling of recombinant DNA systems. The procedures and controls are such as to prevent conventional sampling techniques from being employed during the growth stages of the organisms in question.

For certain tests probes are available which can be installed in openings in a wall of the fermentation tank so as to project into the growth medium and directly interact with that medium. Certain of these probes such as dissolved oxygen concentration and pH are conventionally available which can withstand the sterilization procedure employed prior to inoculation. Probes for other chemical variables such as carbon dioxide and ammonia are not sterilizable. To prevent contamination of the fermenting batch, unsterilized probes can only be used on samples withdrawn from the fermentation tank either continuously or intermittently during the growth of the microorganism.

Continuous sample withdrawal has been attempted using a microporous stainless steel filter which was installed inside the tank. Such stainless steel filters suffered from many disadvantages including very short useful life, and nonuniformity of pore size. The use life of such filters could be increased by enlarging the pore size but this large average size of the pores together with the significant variation in pore size caused the withdrawal of microorganisms from the fermentation tank through the probe which was inconsistent with the rules and procedures on system containment.

It is therefore an object of the present invention to provide a system for the continuous monitoring of the chemistry within a fermentation tank, including contained systems, by which a filtrate free of microorganisms is withdrawn from the culture medium and delivered to assaying means remotely located away from the fermenter. It is a particular object of the present invention to provide within such a system apparatus which will withstand sterilization conditions, will continue to function during the entirety of the fermentation process, and will assure the containment of the system.

In accordance with the present invention, the chemistry of the growth medium can be monitored with the aid of a probe penetrating a wall of the fermenter, the probe including a microporous filtering element for separating a filtrate free of microorganisms from the growth medium. The probe is connected to a conduit and can use a pumping means for pumping the filtrate delivered from the probe through the conduit to appropriate assaying apparatus located exteriorly of the fermenter.

The microporous filtering element can have a pore size of from about 0.001 microns to about 1.0 microns while having a narrow pore size distribution. Preferably the microporous filtering element has an average pore size of about 0.1 microns. The microporous filtering element can have a surface roughness up to about 50 microinches. Preferably the filtering element has a surface roughness of less than about 5 microinches.

Examples of polymeric filtering materials are polymers such as polyvinylidene fluoride, polytetrafluoroethylene, polysulfone, and silicone the preferred polymeric material is polypropylene. Material for constructing such a polymeric filtering element is conventionally available from Membrana, Inc. of Pleasanton, Calif. under the trademark ACCUREL. The manufacturer of microporous products using such materials as disclosed in U.S. Pat. No. 4,247,498 while the manufacture of porous tubing in particular is disclosed in U.S. Pat. No. 4,434,250.

The filtering element can also be composed of an asymetric ceramic material having pores on the outside surface of the required dimension which are tapered or relieved in a manner similar to conventional ultrafiltration membrane type filters. A suitable ceramic material is available from Norton Company of Worcester, Mass. under the trademark CERAFLO.

In the preferred embodiment, the filtering element comprises a tubular segment having one end sealed and the other end communicating with a conduit leading to the assaying apparatus located exterior to the fermenter. The probe includes a plug which is received in an opening of the wall of the fermenter and a support extending from the plug for supporting the tubular filter element, the support including seals at the end of the filtering element such that only a central tubular surface of the filtering element passes filtrate. The plug is generally a threaded element having an aperture therethrough while the support comprises a hollow rod or tube having a plurality of holes spaced along it so as to permit filtrate to pass from the interior of the tubular filtering element into the conduit. Where the filtering element is polymeric, the seals can consist merely of stepped connectors forced into each end of the tubular filtering element, one of the stepped connectors being fixed to the plug coaxially around the support and the other stepped connector including a fixed cap closing the distal end of the connector and filtering element. Where the filtering element is ceramic, the seals can consist of conventional O-rings inserted in a Swagelok fitting or other similar structure.

One feature of the present invention is the use of a material having a small uniform pore size such as will only pass a filtrate free of microorganisms. This material permits the containment of the system during continuous withdrawal of the sample fluid. The pore size is such as will prevent microorganisms from traversing the material in either direction and hence contamination of the inoculated medium is also prevented by use of this same material.

Another feature of the present invention is the surface roughness of the preferred materials being less than about 5 microinches. This surface character is such as to permit the same probe to be used during the entire incubation period as this character aids in the nonadhesion of bacteria, micellae, and other solids even where the probe is subjected to only modest flow turbulence. A preferred use of the probe in a fermenter would include the positioning of such a probe within the fermenter such that the growth medium immediately surrounding the probe is undergoing turbulent flow so as to aid in the maintenance of the surface of the filtering element substantially free from obstruction.

An additional feature of the present invention is the sterilizable character of the probe as a whole since all of the materials including the microporous element are capable of withstanding the steam sterilization typically employed prior to inoculation of the fermenter. The present invention has the advantage that all direct sensing instrumentation other than the sampling probe itself can be placed exterior of the fermenter and need not undergo sterilization. This permits a wider range of variables to be continuously monitored with instruments after having much lower cost that the same instrument when sterilizable.

Additional features and advantages of the invention will become apparent to those skilled in the art upon consideration of the following detailed description of a preferred embodiment exemplifying the best mode of carrying out the invention as presently perceived. The detailed description particularly refers to the accompanying figures in which.

Figure 1:
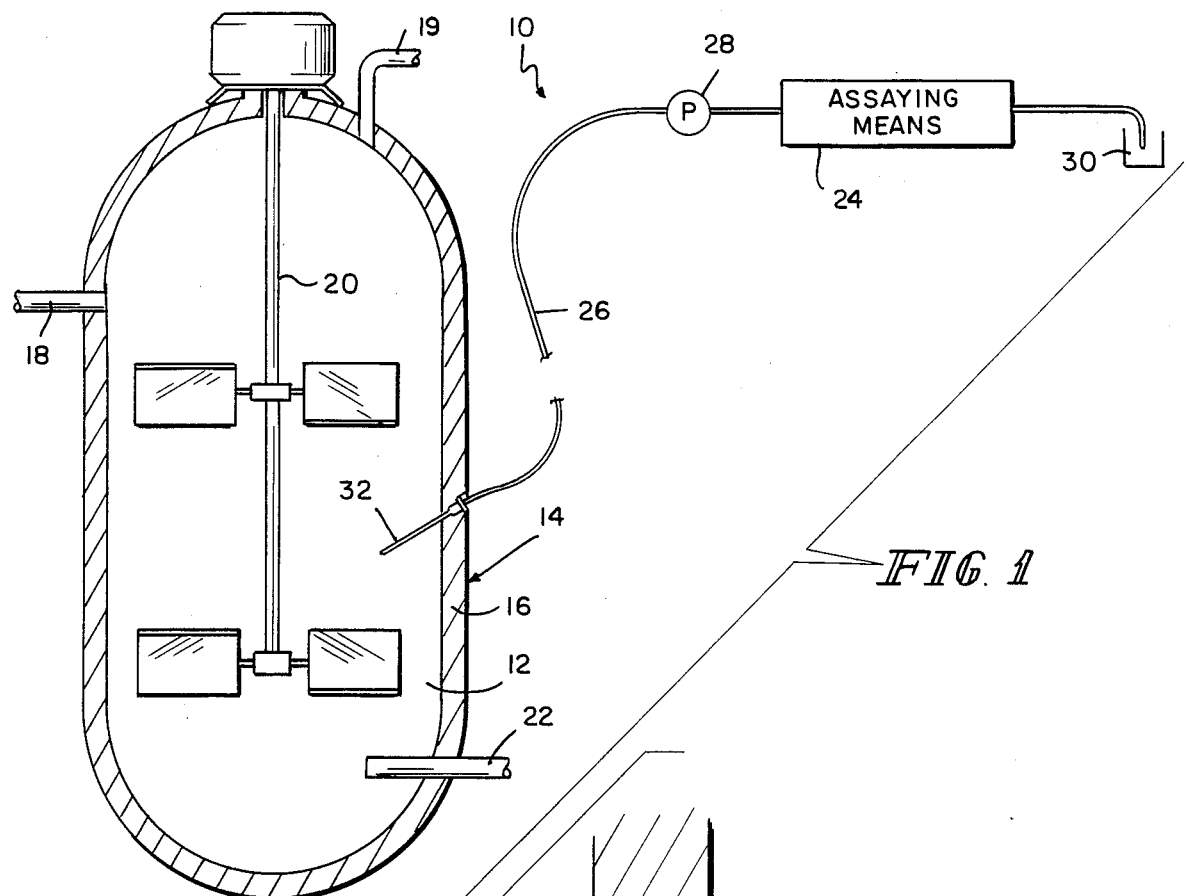
FIG. 1 is a schematic view of an industrial fermenter having a probe installed in accordance with the present invention.
Figure 2:
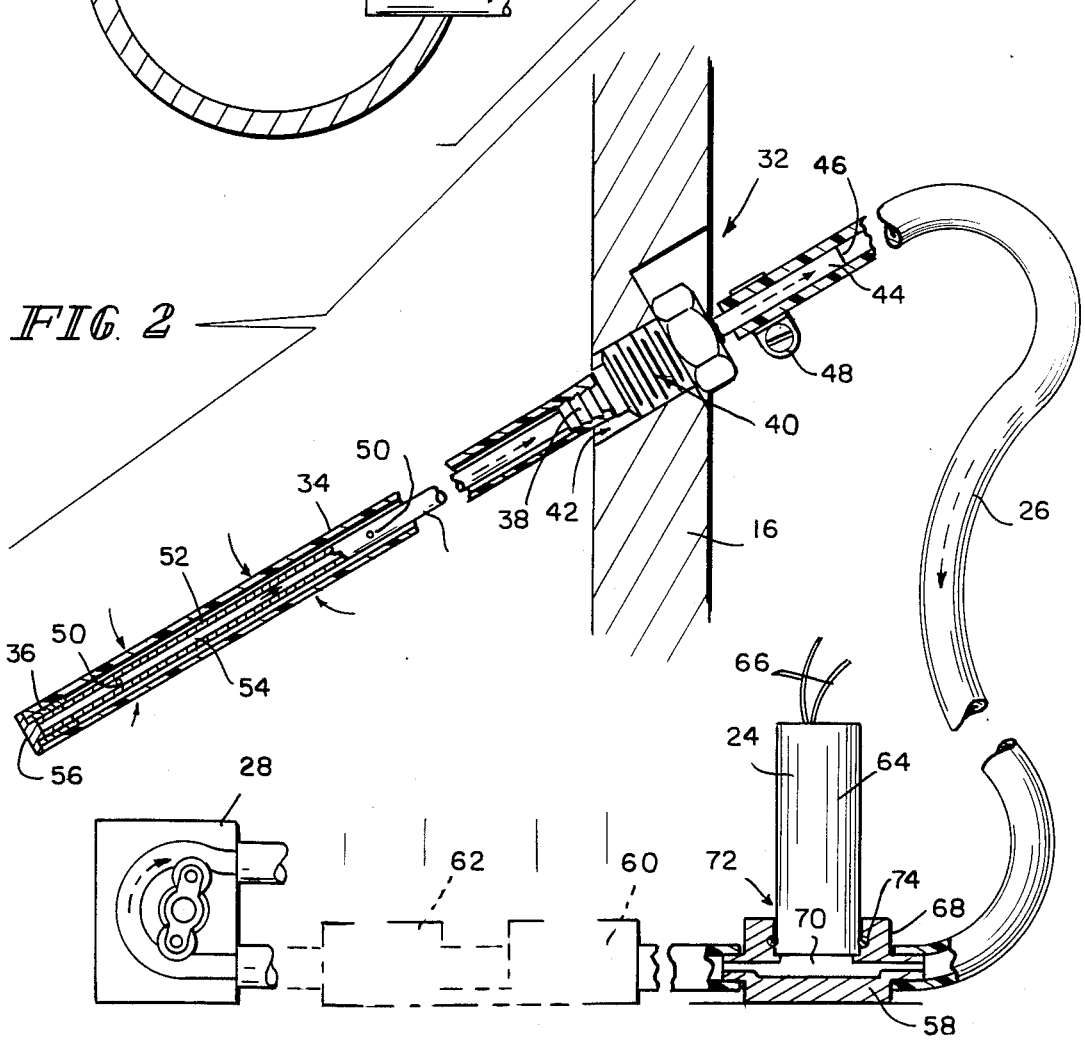
FIG. 2 is a further detailed view of the probe and associated apparatus by which the chemistry of the growth medium within the fermenter can be continuously monitored.

Apparatus in accordance with the present invention is shown in FIGS. 1 and 2. The system 10 is adapted to continuously monitor the chemistry of a cultured or growth medium 12 within a fermenter 14. The fermenter 14 includes a containment vessel 16. The fermenter is connected to appropriate supplies 18 for supplying the growth medium from mixing tanks (not shown). An agitator 20 is provided which acts to continuously circulate the growth medium within the fermenter. In a typical system, additional sources 22 are provided for the introduction of sterile air or other growth promoting gases. A vent 19 is typically provided to permit release of gasses. The temperature of the fermenter is typically controlled by circulating water through a jacket or coil (not shown). The supply 18 can be connected to various auxiliary tanks (not shown), for providing the addition of nutrients during the growth cycle as well as acid or base to control pH, antifoaming agents, growth stimulants, special minerals, etc.

The monitoring system 10 comprises generally an assaying means 24 and a conduit 26 leading from the assaying means to the fermenter 14. A pump 28 can be provided for pumping material through the conduit 26 to the assaying means 24. Alternatively, gas pressure within the tank 16 can be employed to cause the desired flow. After the withdrawn material is assayed, it may be disposed of in an appropriate receptacle 30. The system 10 also includes a probe 32 connected to conduit 26 which penetrates a wall 16 of the fermenter 14.

The probe 32 is shown in more detail in FIG. 2 and comprises generally a tubular filtering element 34 composed of one of the materials previously discussed. The tubular filtering element 34 is closed on each end by seals 36 and 38 which are shown to consist of stepped connectors over which the tubular element 34 is forced. The seal 38 is welded or otherwise secured to a threaded plug 40 which is removably received in aperture 42 in wall 16 of the fermenter 14. The plug 40 includes a hole or aperture (not shown) through which a length of stainless steel tubing 44 projects. The conduit 26 is secured to the outer end 46 of tubing 44 by clamp 48 or other equivalent means.

That portion of the stainless steel tube 44 which projects inside the fermenter 14 can include a series of spaced apertures 50 which permit filtrate to pass from the space 52 between the supporting tube 44 and the tubular filtering element 34 into the interior 54 of tube 44. The seal 36 includes an end cap 56 which prevents the intrusion of materials through the distal end of the tubular element 34.

Between batches, the probe 32 can be easily removed from the fermenter 14 to allow inspection, cleaning or replacement of the filtering element 34, and thereafter be reinstalled in a very short time.

The filtrate is withdrawn from the fermenter through the tubular filtering element 34 by the pressure in the tank 16 or by the pumping means 28 shown in FIG. 2 to be a peristaltic pump. The filtrate can travel through one or more assaying locations 58, 60, 62 which may be arranged in series and/or parallel where various tests can be conducted on the filtrate removed. The sensors 64 are connected by wires 66 or other equivalent means such as optical fibers to indicators not shown and subject the withdrawn filtrate to various tests and measurements by which the chemistry of the fermentation process can be continuously monitored and controlled. Each of the assaying locations 58, 60, 62 can advantageously comprise a stainless steel block 68 having a passageway 70 therethrough including an opening 72 into which the particular instrument 64 is received. Appropriate sealing means 74 such as an O ring can be included to assure that the system as a whole is maintained in a generally sealed condition so as to assure continuity of operation.

EXAMPLE I

A probe was constructed in accordance with the present invention utilizing a filtering element consisting of a 20 cm length of ACCUREL polypropylene tubing having an inside diameter of 5.5 mm, an outside diameter of 8.6 mm a surface roughness of about 5 microinches, and a nominal pore size of 0.1 microns. It was installed in a contained system for the growth of recombinant DNA modified *Escherichia coli*. After sterilization and innoculation, the filtrate was withdrawn over the entire growth period of one day at a rate of approximately 100 milliliters per hour with no noticeable drop in flow rate. At the end of the growth period the *E. coli* were harvested and the process repeated for seven days without removal of the probe. The withdrawn filtrate was subjected to a test for enzyme concentration during each growth cycle. The results of the tests were employed to modify the growth medium content from time to time during the growth cycle as required. No decline in flow rate or other variation in performance was observed.

The filtrate was also subjected to a conventional test which would identify the presence of microorganisms in the filtrate. The filtrate was demonstrated to be free from living microorganisms thereby assuring containment of the DNA modified *E coli* within the fermenter.

EXAMPLE II

A probe constructed in accordance with Example I was employed in a penicillin V fermentation. A filtrate was withdrawn through the probe over the entire fermentation period of seven days at a flow rate of about 50 ml/hr. with no noticeable drop in flow over the entire period. No surface fouling of the probe was observed. The filtrate was subjected to tests for dissolved oxygen, pH, ammonia, and glucose. The test results were employed to modify the growth medium content from time to time during the period.

EXAMPLE III

A probe was constructed in accordance with the present invention using a 25 cm length of CERAFLO layered ceramic tubing having an outside diameter of about 5 mm, an inside diameter of about 3 mm, a nominal surface pore size of about 0.1 microns and a surface roughness of about 40 microinches. The probe was installed in a penicillin V fermentation similar to Example II and filtrate withdrawn at a flow rate of about 30 ml/hr. The performance and test results were similar to those observed for Example II.

Although the invention has been described in detail with reference to preferred embodiments and specific examples, variations and modifications exist within the scope and spirit of the invention as described and as defined in the following claims.

I claim:

1. A system for continuously monitoring the chemistry of a liquid medium within a container comprising an assaying means located exteriorly of the container, a conduit connected to the assaying means and leading to the container, a probe connected to the conduit and penetrating a wall of the container, the probe including a microporous filtering element for separating a filtrate from the culture medium, the filtering element having a surface roughness less than about 50 microinches, and means for delivering the filtrate from the probe through the conduit to the assaying means.

2. The system of claim 1 wherein the container includes a stirring mechanism for causing circulation of the medium within the container, the probe being situated within the container such that the medium immediately surrounding the probe is undergoing turbulent flow.

3. The system of claim 1 wherein the microporous filtering element has pore size of from about 0.001 to about 1.0 microns while having a narrow pore size distribution.

4. The system of claim 3 wherein the microporous filtering element has an nominal pore size of about 0.1 microns.

5. The system of claim 1 wherein the filtering element comprises a tubular member having one end sealed and the other end communicating with the conduit.

6. The system of claim 1 wherein the probe further comprises a plug received in an opening of a wall of the container, a support means extending inward from the plug for supporting the filtering element, and sealing means on each end of the support means for sealing the ends of the filtering element such that only a central tubular surface of the filtering element can pass filtrate from the liquid medium.

7. The system of claim 6 wherein the plug comprises a threaded element having an aperture therethrough, the support means being received in the aperture and comprising a hollow rod having a plurality of holes spaced therealong.

8. The system of claim 6 wherein the support means comprises a tubular member having an outside diameter less than the inside diameter of the tubular filtering element, the tubular filtering element extending over substantially the whole of the length of the support means.

9. The system of claim 6 wherein the sealing means comprises stepped connectors forced into each end of the filtering element, one of the stepped connectors being fixed to said plug coaxially around the supporting means and the other stepped connector includes a fixed cap closing the end of the connector and filtering element.

10. An apparatus for continuously withdrawing a sample of the soluable portion of a liquid medium from a contained recombinant DNA system fermenter comprising a plug received in an opening of a wall of the fermenter, a support means extended inward from the plug for supporting a filtering element, a tubular microporous filtering element extending over a major portion of the length of the support means, sealing means at each end of the support means for sealing the ends of the filtering element such that only a tubular surface of the filtering element can pass filtrate from the medium into the apparatus, the tubular surface having a nominal pore size of less than about 0.1 microns and a surface roughness of less than about 50 microinches.

11. The apparatus of claim 10 wherein the plug includes connecting means for permitting removal of the plug from the wall of the fermenter to allow inspection of the filtering element.

* * * * *